(12) United States Patent
Warkentin

(10) Patent No.: US 10,751,439 B2
(45) Date of Patent: Aug. 25, 2020

(54) VENT BALLOON

(71) Applicant: William Paul Warkentin, West Bloomfield, MI (US)

(72) Inventor: William Paul Warkentin, West Bloomfield, MI (US)

( * ) Notice: Subject to any disclaimer, the term of this patent is extended or adjusted under 35 U.S.C. 154(b) by 186 days.

(21) Appl. No.: 15/853,093

(22) Filed: Dec. 22, 2017

(65) Prior Publication Data

US 2018/0326110 A1 Nov. 15, 2018

Related U.S. Application Data

(60) Provisional application No. 62/504,839, filed on May 11, 2017.

(51) Int. Cl.
*A61L 9/12* (2006.01)
*A63H 27/10* (2006.01)

(52) U.S. Cl.
CPC .............. *A61L 9/12* (2013.01); *A63H 27/10* (2013.01); *A61L 2209/16* (2013.01); *A63H 2027/1025* (2013.01); *A63H 2027/1041* (2013.01); *A63H 2027/1083* (2013.01)

(58) Field of Classification Search
CPC ........................................................ A61L 9/12
See application file for complete search history.

(56) References Cited

U.S. PATENT DOCUMENTS

| | | | | |
|---|---|---|---|---|
| 3,149,017 A | * | 9/1964 | Ehrreich | B29C 71/04 244/31 |
| 5,186,675 A | * | 2/1993 | Stoddard | A63H 3/06 40/212 |
| 7,381,112 B1 | * | 6/2008 | Symes | A63H 33/26 40/410 |
| 7,905,426 B1 | * | 3/2011 | Greiner | A61L 9/122 239/44 |
| 2007/0249259 A1 | * | 10/2007 | Pham | A63H 5/00 446/224 |
| 2016/0238275 A1 | * | 8/2016 | Rasmussen | F24F 13/084 |
| 2017/0043046 A1 | * | 2/2017 | Martin | A61L 9/12 |

* cited by examiner

*Primary Examiner* — Donald R Spamer
(74) *Attorney, Agent, or Firm* — Kohn & Associates, PLLC

(57) ABSTRACT

A vent balloon for use over an air vent including an inflatable body operatively attached to a base on a proximal side, and a removable adhesive attached to a distal side of the base for attaching to an air vent. A method of using a vent balloon by removably adhering an inflatable body of the vent balloon through a base to an air vent, flowing air through the inflatable body, and inflating the inflatable body. A vent balloon for dispersing scent in a room, including an inflatable body operatively attached to a base on a proximal side, a removable adhesive attached to a distal side of the base for attaching to an air vent, and at least one scent mechanism operatively attached to the vent balloon for dispersing scent in the room. A method of dispersing scent in a room using the vent balloon.

33 Claims, 17 Drawing Sheets

VENT BALLOON

BACKGROUND OF THE INVENTION

1. Technical Field

The present invention relates to balloons and inflatable objects. More specifically, the present invention relates to balloons for use over air vents.

2. Background Art

Balloons are used by many people for festive events and parties such as for birthdays, graduations, anniversaries, baby showers, retirements, and holidays. Helium balloons can be filled at a store but then must be transported to the home or event site in a car and can be cumbersome. Other standard balloons can be filled by blowing air at the home, but this can also be difficult and tiresome.

A balloon has been designed to fit over an air vent to be inflated by air flowing out of the air vent. U.S. Pat. No. 5,186,675 to Stoddard discloses an inflatable vent toy for an exhaust vent air outlet including an inflatable balloon made of a flexible material patterned and shaped to suit the preference of a user having a base defining an air inlet with surrounding attachment structure to secure the base over the exhaust vent air outlet such that the air inlet is in communication with the vent air outlet to enable in-coming air from the vent to enter the base air inlet and fill the balloon in a first mode, and to escape and collapse in a second mode when the in-coming air from the vent stops. The base structure is generally removably attached to the vent with magnets, ties, hooks, or straps. The inflatable vent toy can be in shapes such as a ghost or goblin, or contain pictures of athletes or movie characters.

There are several disadvantages to using a vent balloon with a base of corrugated cardboard, such as product liability using over a hot air vent, and the cheap looking quality of the cardboard. Therefore, there remains a need for a balloon that is easy to use in the home that can effectively make use of air from an air vent that is also safe to use.

SUMMARY OF THE INVENTION

The present invention provides for a vent balloon for use over an air vent including an inflatable body operatively attached to a base on a proximal side, and a removable adhesive attached to a distal side of the base for attaching to an air vent.

The present invention provides for a method of using a vent balloon by removably adhering an inflatable body of the vent balloon through a base to an air vent, flowing air through the inflatable body, and inflating the inflatable body.

The present invention provides for a vent balloon for dispersing scent in a room, including an inflatable body operatively attached to a base on a proximal side, a removable adhesive attached to a distal side of the base for attaching to an air vent, and at least one scent mechanism operatively attached to the vent balloon for dispersing scent in the room.

The present invention also provides for a method of dispersing scent in a room, by removably adhering an inflatable body of a vent balloon through a base to an air vent, flowing air through the inflatable body and over at least one scent mechanism, releasing scent into the air, inflating the inflatable body, and flowing scented air through vents on the inflatable body into the room.

DESCRIPTION OF THE DRAWINGS

Other advantages of the present invention are readily appreciated as the same becomes better understood by reference to the following detailed description when considered in connection with the accompanying drawings wherein.

DETAILED DESCRIPTION OF THE INVENTION

Figure 1:
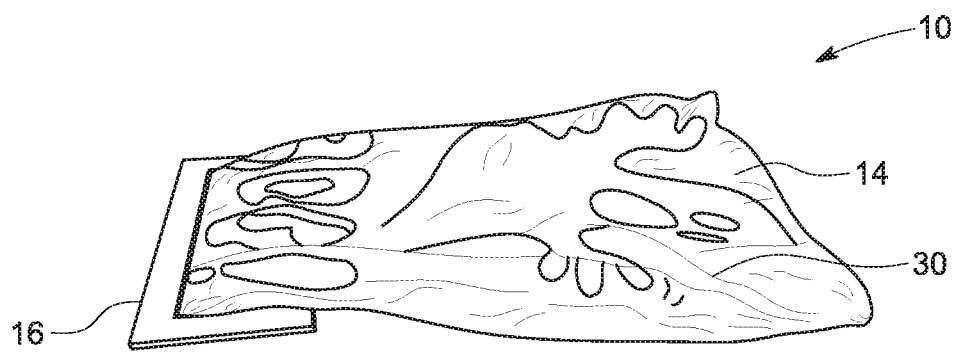
FIG. 1 is a photograph of a vent balloon of the present invention.
Figure 2:
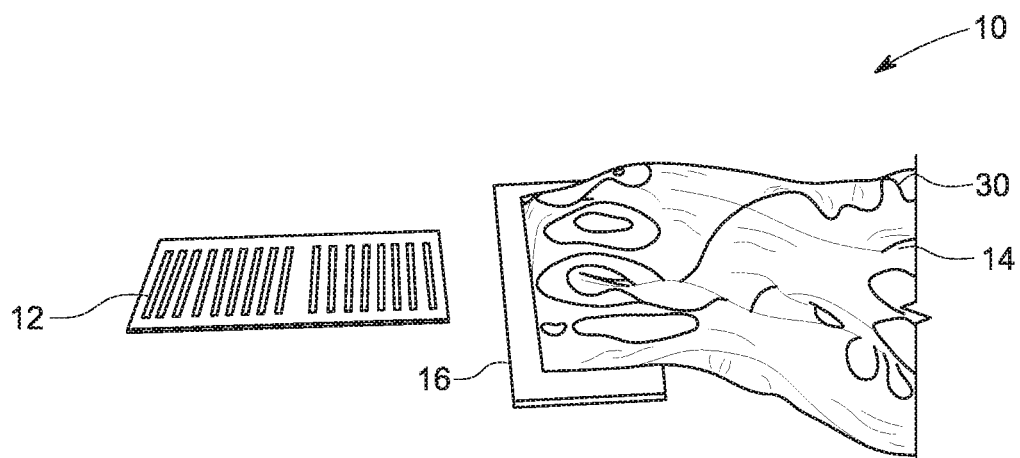
FIG. 2 is a photograph of the vent balloon beside an air vent.
Figure 3:
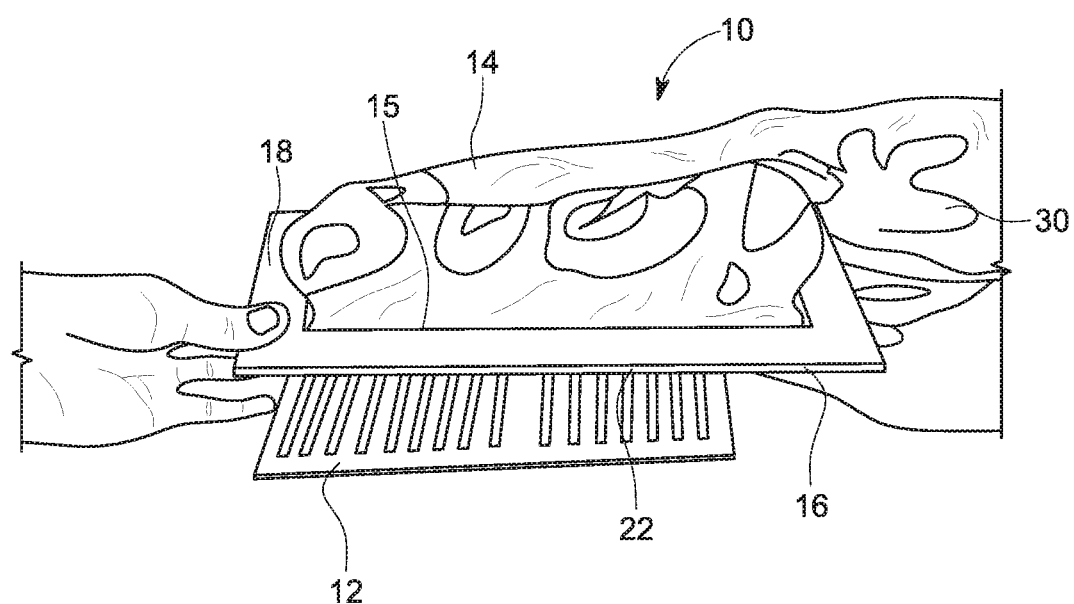
FIG. 3 is a photograph of placement of the vent balloon over the air vent.
Figure 4:
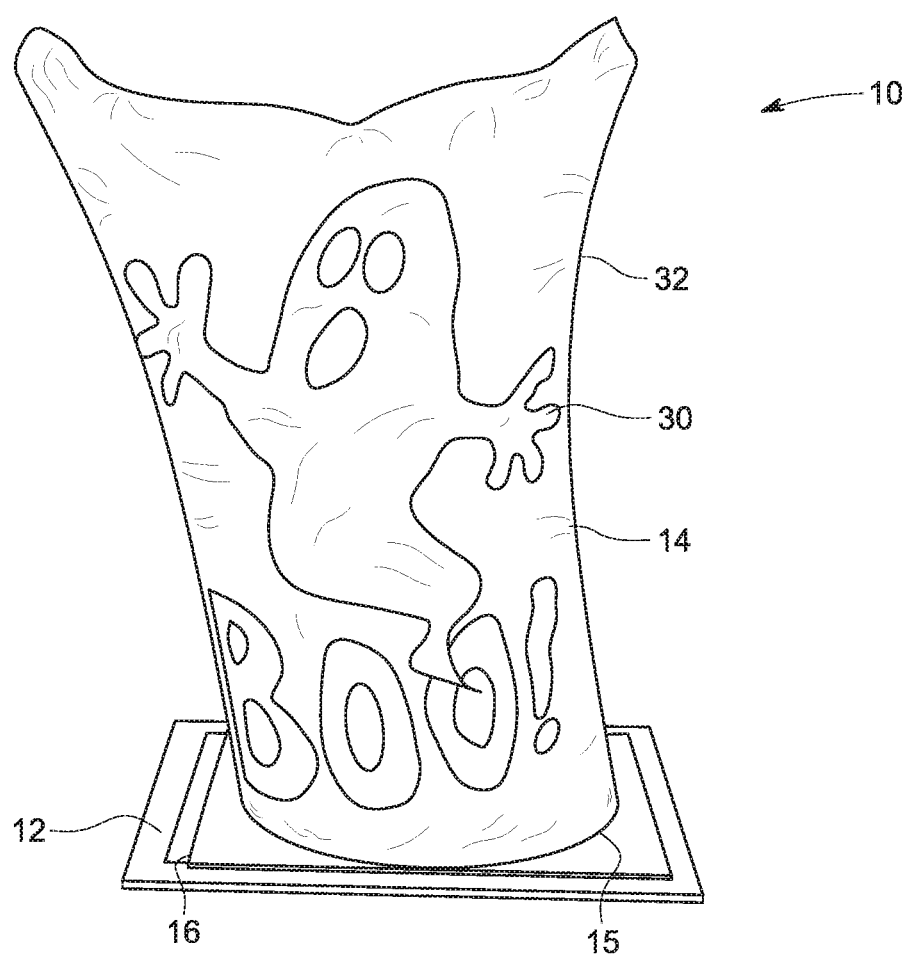
FIG. 4 is a photograph of the vent balloon inflated and positioned over the air vent.

The present invention provides for a vent balloon, shown at 10 in the FIGURES, that is inflatable by either cold or hot air flowing through an air vent 12 when placed over the air vent 12. The vent balloon 10 includes an inflatable body 14 operatively attached to a base 16 on a proximal side 18, and a removable adhesive 20 attached to a distal side 22 of the base 16.

Figure 5:
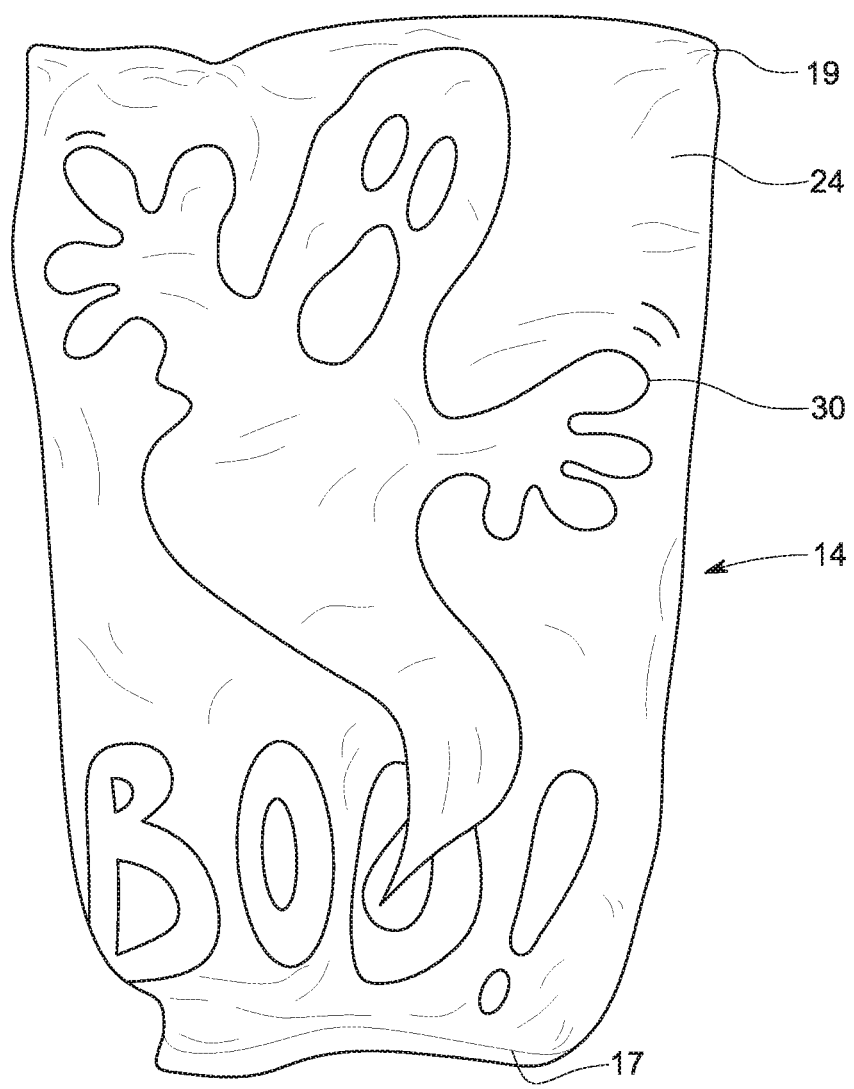
FIG. 5 is a photograph of a lay-flat polyethylene bag.
Figure 8A:
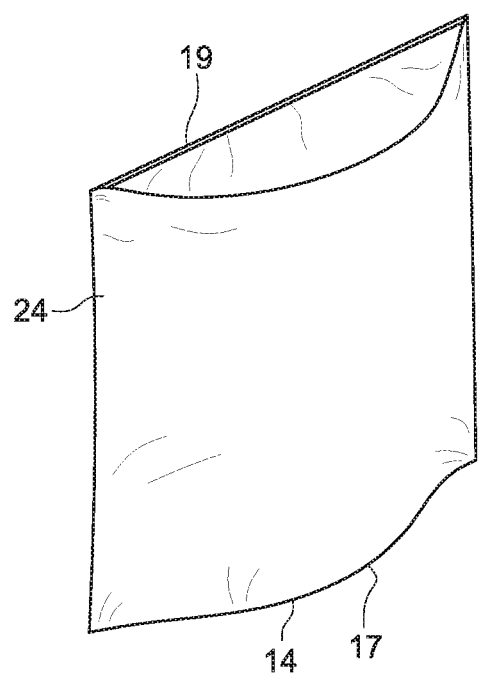
FIG. 8A is a schematic of a lay-flat polyethylene bag and FIG. 8B is a photograph of an inflated lay-flat polyethylene bag vent balloon.
Figure 8B:
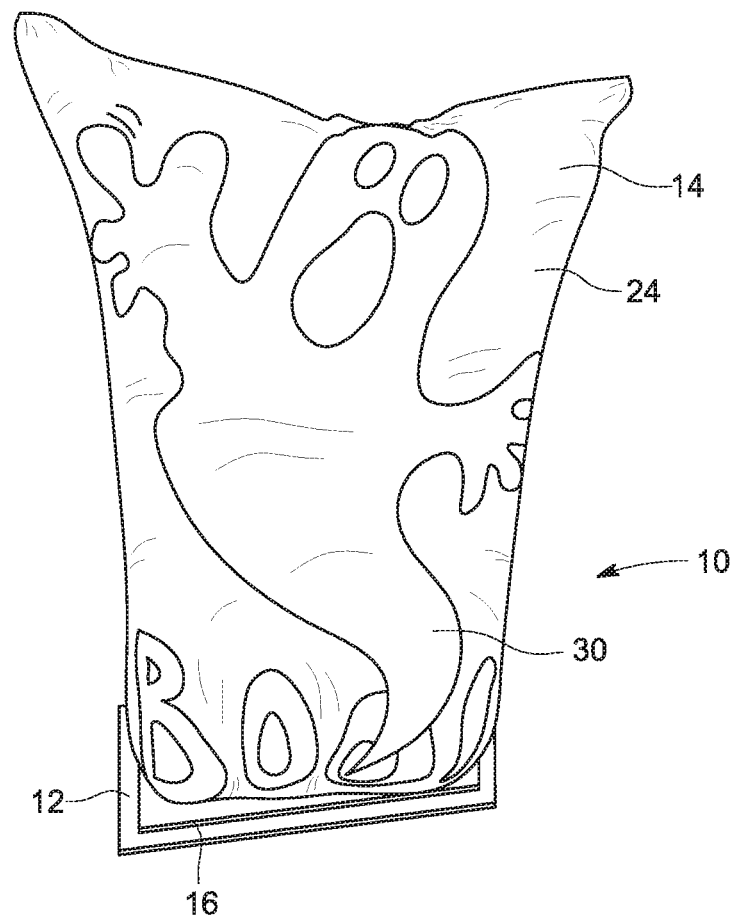
Figure 9A:
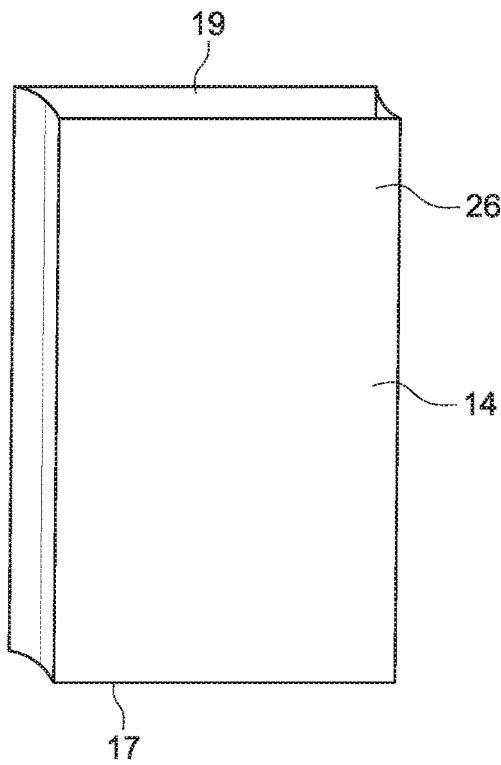
FIG. 9A is a schematic of a gusseted polyethylene bag and FIG. 9B is a side perspective view of an inflated gusseted polyethylene bag vent balloon.
Figure 9B:
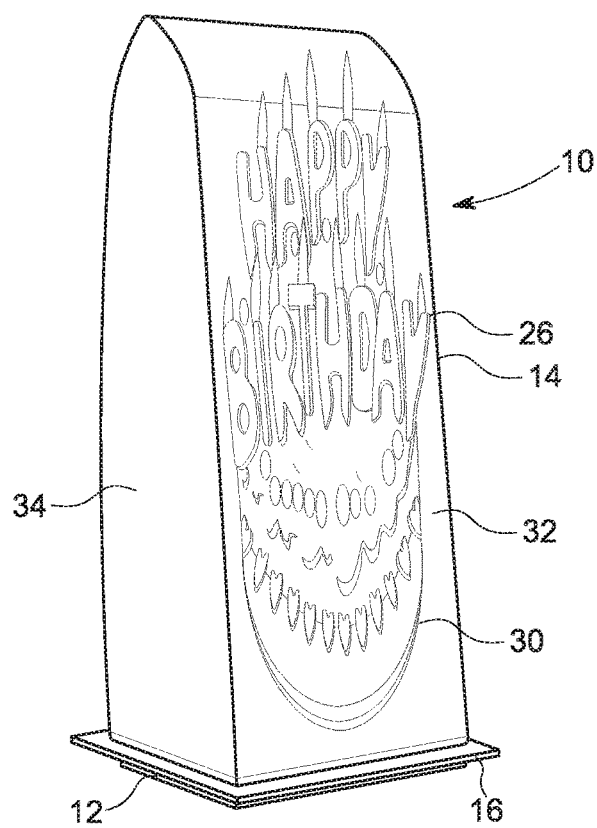
Figure 13:
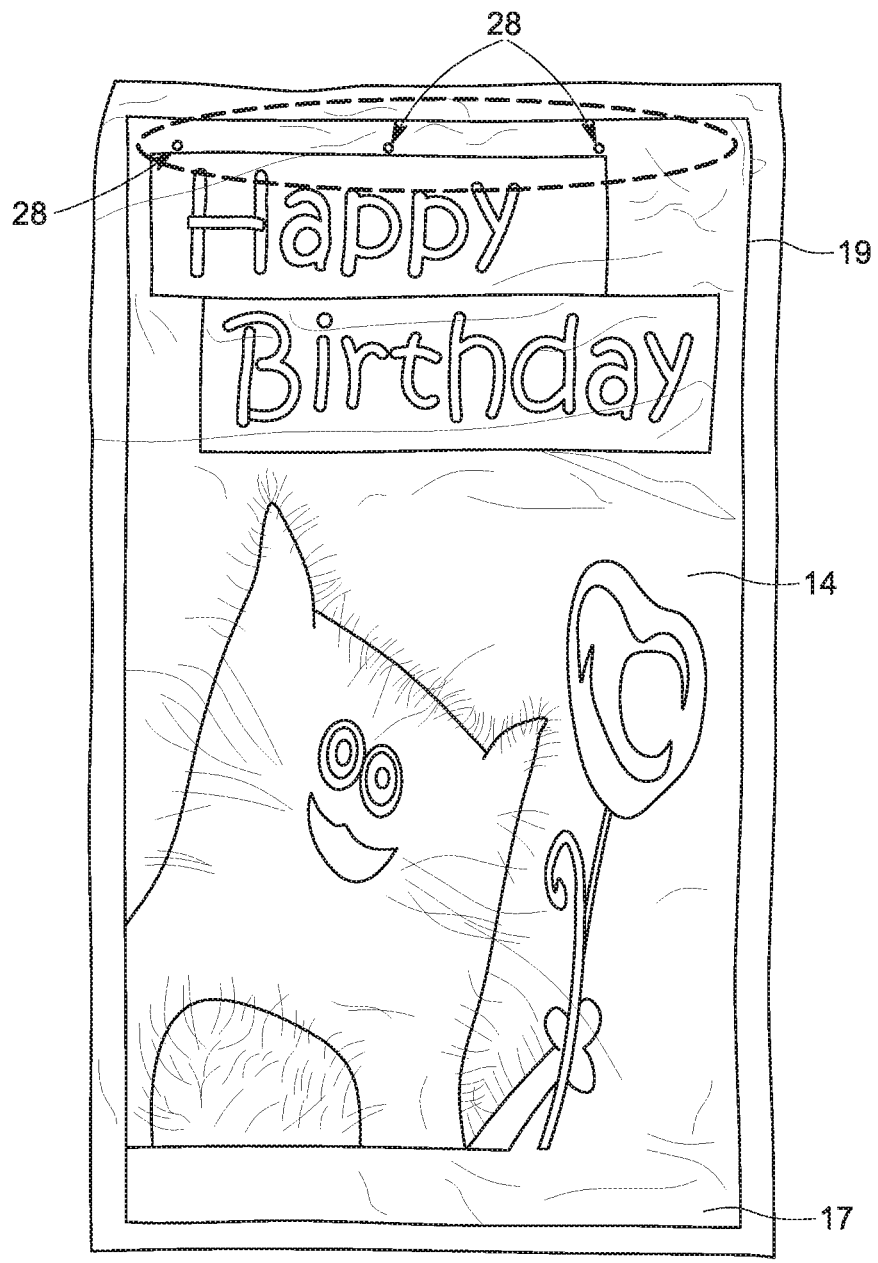
FIG. 13 is a front view of the inflatable body with vents.

The inflatable body 14 is preferably a polyethylene bag having an open end 17 and a closed end 19. The open end 17 is operatively attached to the base 16 with an air tight seal. In one embodiment, the inflatable body 14 is a lay-flat polyethylene bag 24, shown in FIGS. 1-5, 7, and 8A-8B. The lay-flat polyethylene bag 24 is shown without the base 16 in FIGS. 5 and 8A. In another embodiment, the inflatable body 14 is a gusseted polyethylene bag 26, shown in FIG. 9A without the base 16 and in FIG. 9B with the base 16. The inflatable body 14 can include at least one vent 28 that can essentially be a slit in the inflatable body 14 at any suitable location in order to let air gradually release from and flow through the vent balloon 10 while still allowing the inflatable body 14 to stand upright, shown in FIG. 13. Various sizes of the vent balloon 10 can have different numbers of vents 28. For example, a 20" tall inflatable body 14 can have three vents 28 or four vents 28, each ¼" diameter in size, in a row near the closed end 19 of the inflatable body 14. A 26" tall inflatable body 14 can have three vents 28 or four vents 28, each ½" diameter in size. A 30" tall inflatable body 14 can have three vents 28 or four vents 28, in any suitable diameter size.

The inflatable body 14 further includes a design 30 imprinted on a front side 32 or on both the front side 32 and a back side 34. The design 30 can be the same on the front side 32 and back side 34, or different on each side 32, 34. The design 30 can be a holiday greeting, congratulations, a personal message, cartoon characters, general celebratory designs, or promotional advertisements. The inflatable body 14 can also be any desired color (including metallics) and the design 30 can be any desired color.

Figure 11A:
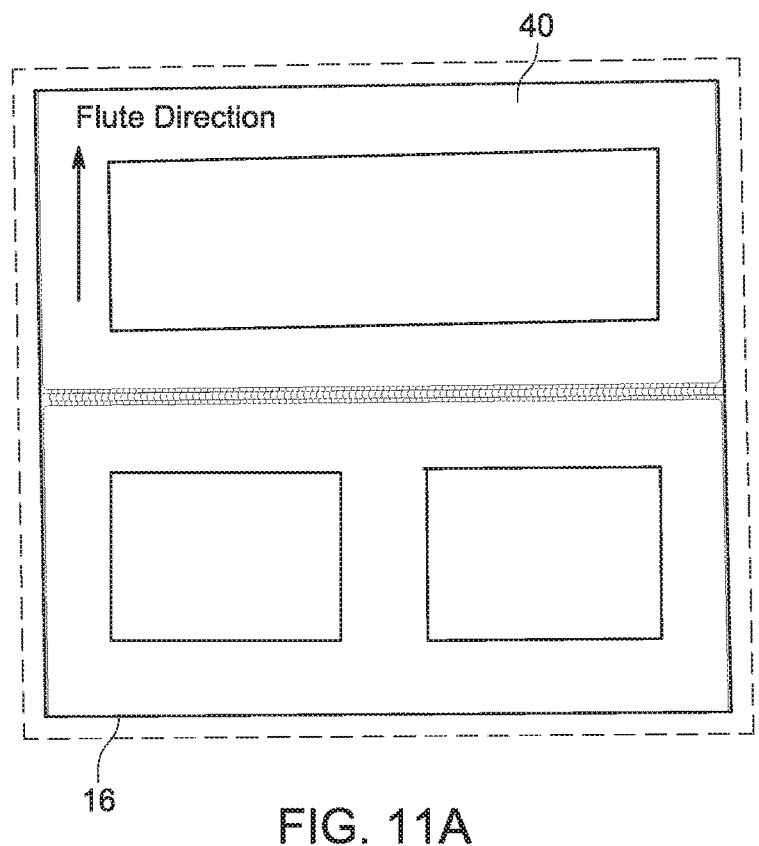
FIGS. 11A and 11B are top views of a base with different flute directions.
Figure 11B:
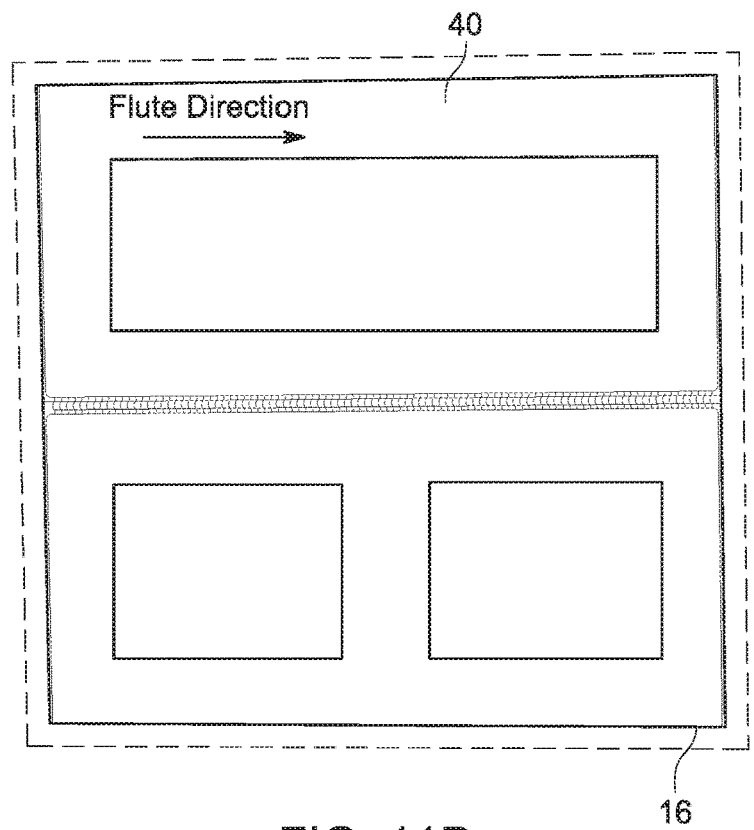

The inflatable body 14 is operatively attached to the base 16 entirely at a bottom end 15 by an adhesive glue or any other suitable mechanism. The base 16 is shown in FIGS. 1-5, 6-7, 8B, and 9B. The base 16 is preferably made of corrugated cardboard, corrugated plastic (fluted polypropylene plastic), or molded plastic that is die cut. Preferably, the base 16 is made from 2.5 mm thick fluted polypropylene plastic. The base 16 can have flutes 40 that preferably run in a vertical direction, shown in FIG. 11A. This allows for the mailing of the vent balloon 10 to be in a flexible package, reducing mailing costs. Less preferably, the base 16 can have flutes 40 running in a horizontal direction, shown in FIG. 11B, however, this would increase mailing costs. The base 16 can be any suitable shape and size to fit over and adhere to standard air vents 12, and preferably in a rectangular shape. The vent balloon 10 can also preferably be sized to fit inside a 11.5" by 5.25" envelope for mailing through regular mail processing.

Figure 6A:
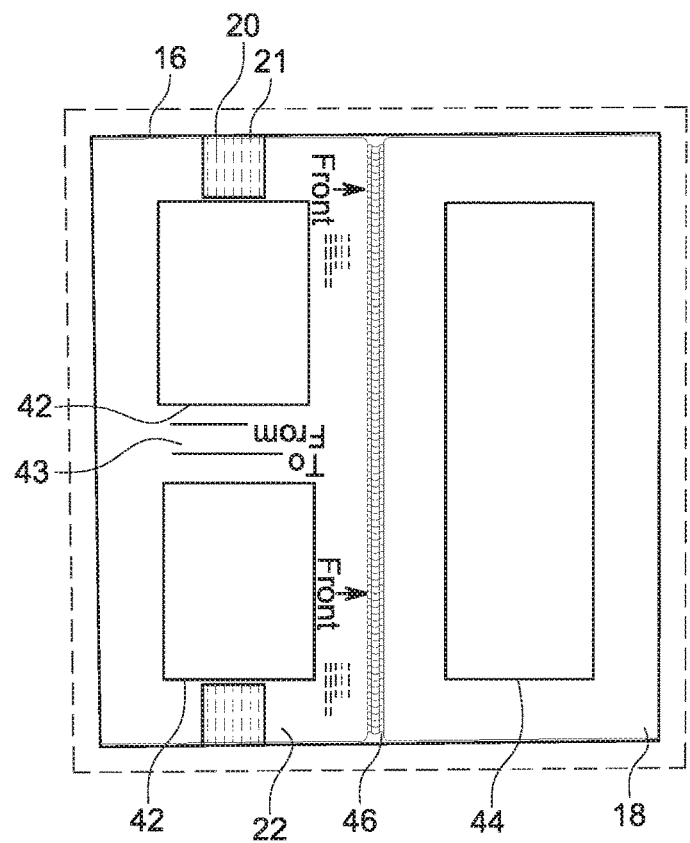
FIGS. 6A-6G are views of the assembly of the base with the inflatable body.
Figure 6B:
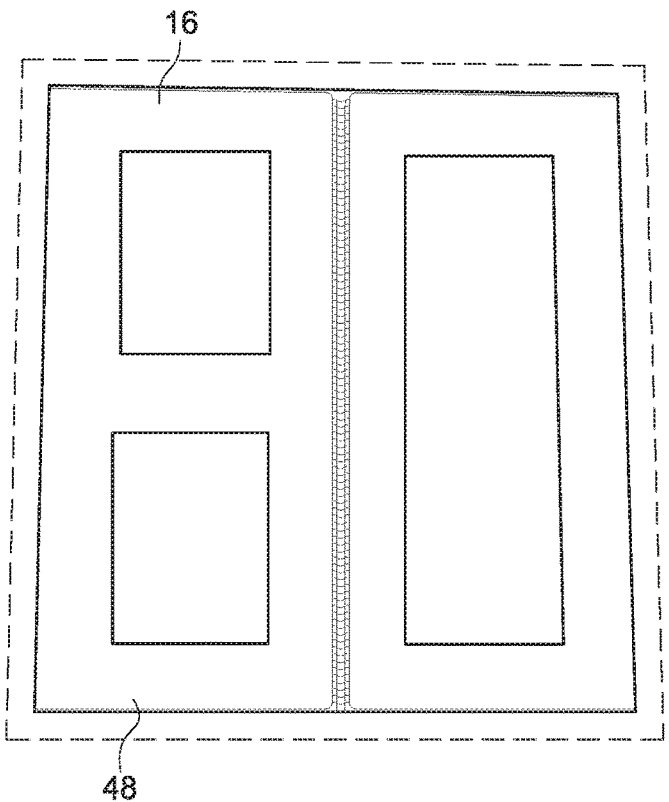
Figure 6C:
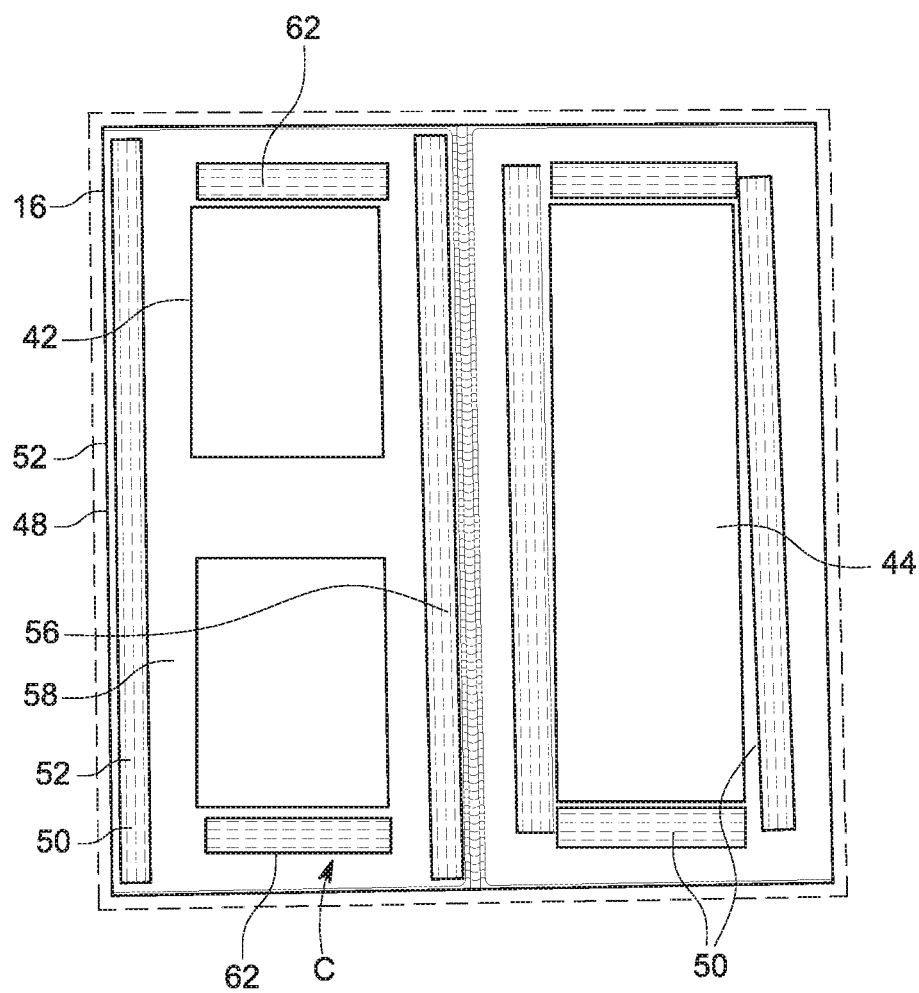

The base 16 can be manufactured as shown in FIGS. 6A-6G and then folded into a rectangular shape. FIG. 6A shows the distal side 22 of the base 16 and the proximal side 18, joined at a center seam 46. The distal side 22 can include at least one distal facing cutout 42 (two are shown in the FIGURES separated by a central bar 43), and the proximal side 18 can include a proximal facing cutout 44. FIG. 6B shows an inner side 48 of the base 16 before an inner adhesive 50 has been applied. FIG. 6C shows the inner side 48 after inner adhesive 50 has been applied, which can be an adhesive tape with a protective liner 52 or hot melt glue. The inner adhesive 50 secures the inflatable body 14 to the base 16. The inner adhesive 50 can be located in any suitable position to secure the inflatable body 14, but preferably surrounding the proximal facing cutout 44 and an inner edge 54 and outer edge 56 of the inner distal side 58 as shown in FIG. 6C. Additional filter or scent mechanism adhesives 60 can also be included on the inner distal side 58.

Figure 6D:
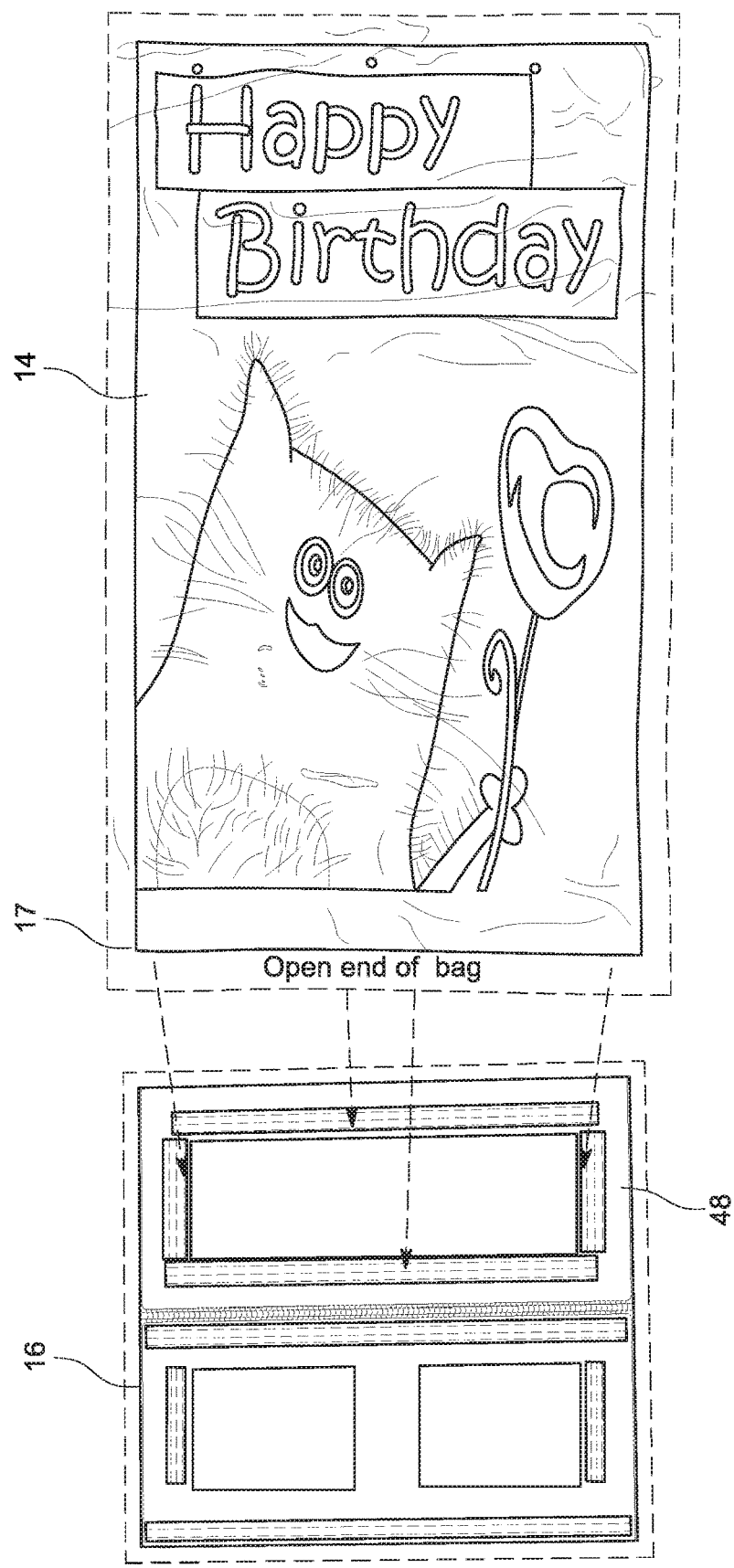
Figure 6E:
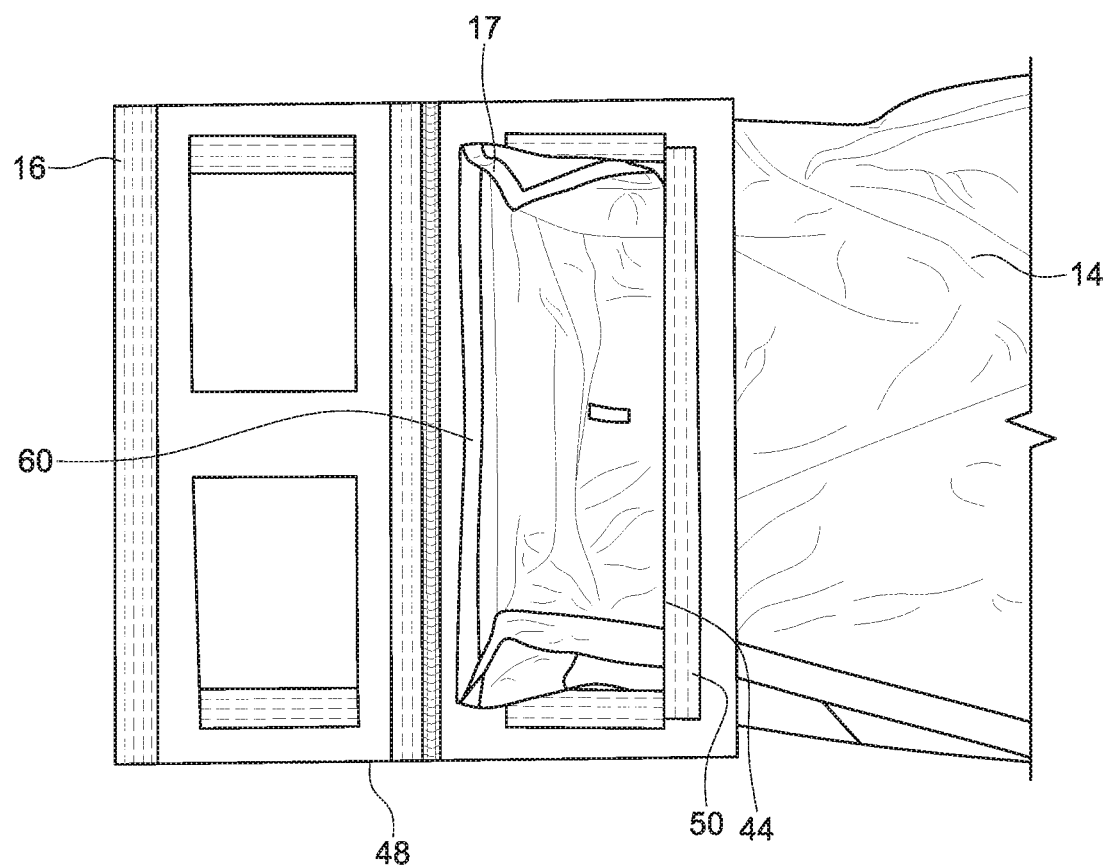
Figure 6F:
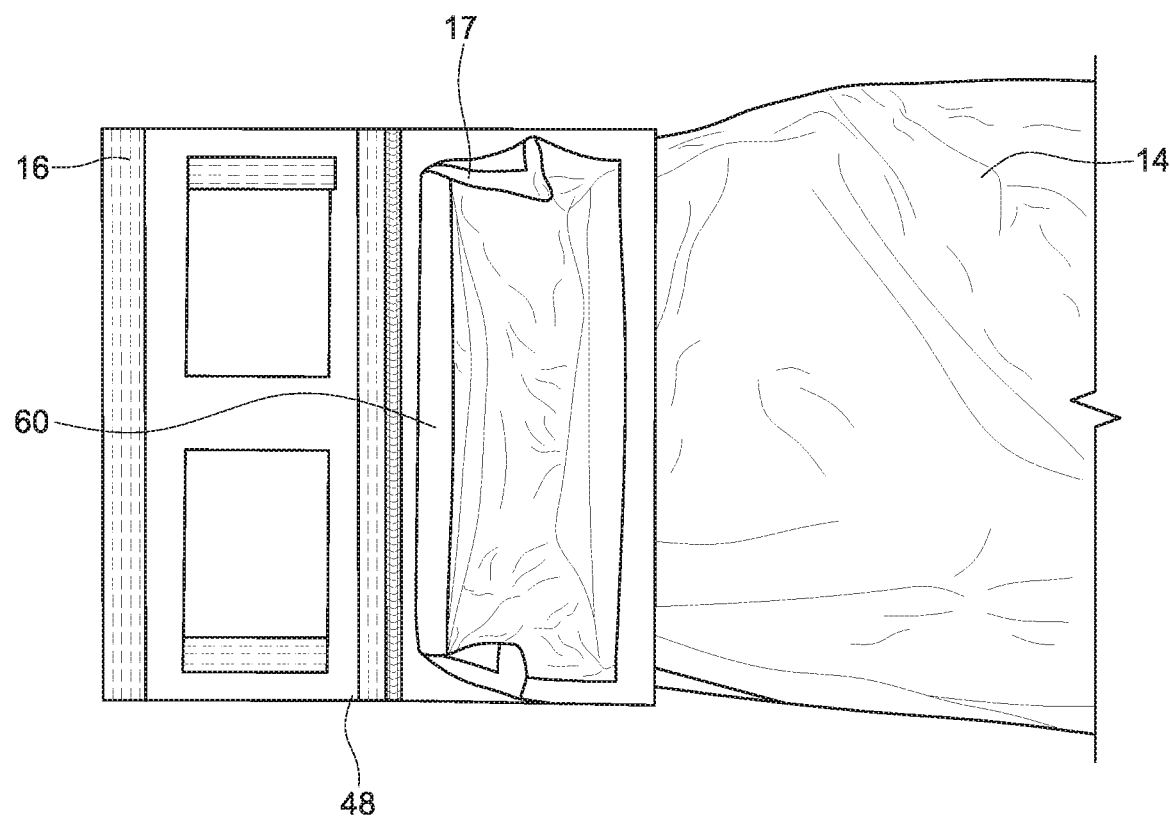
Figure 6G:
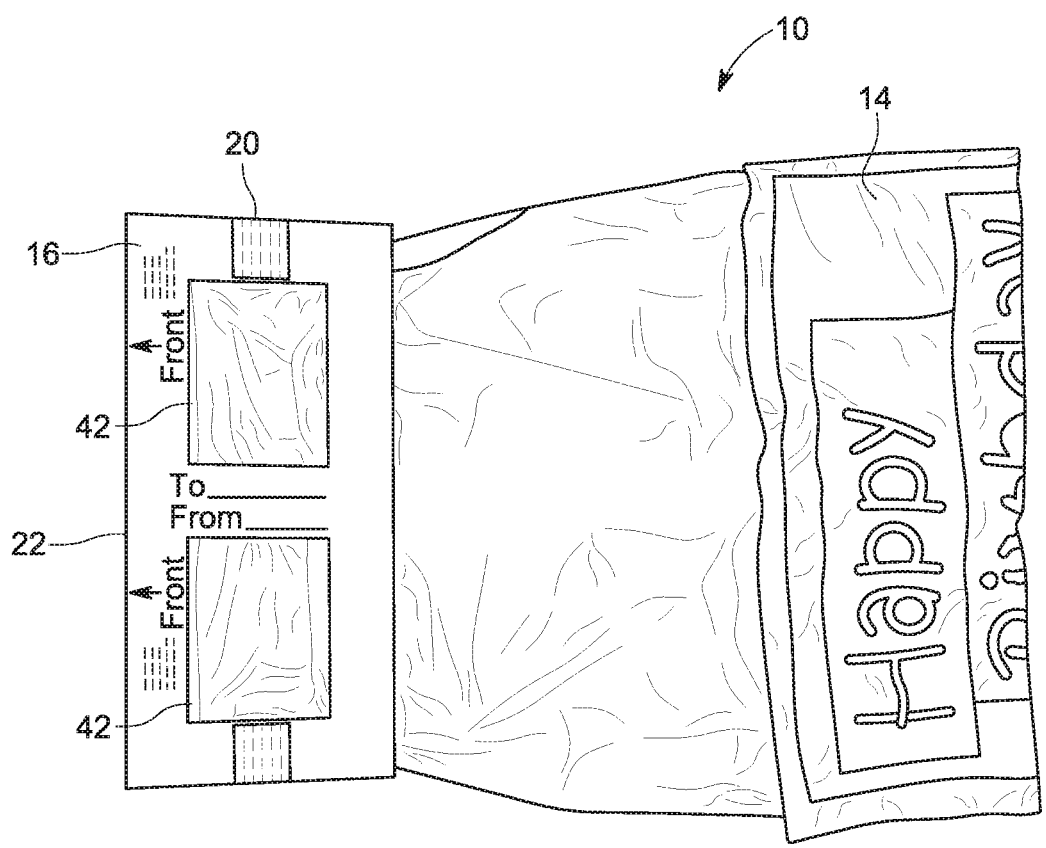
Figure 7:
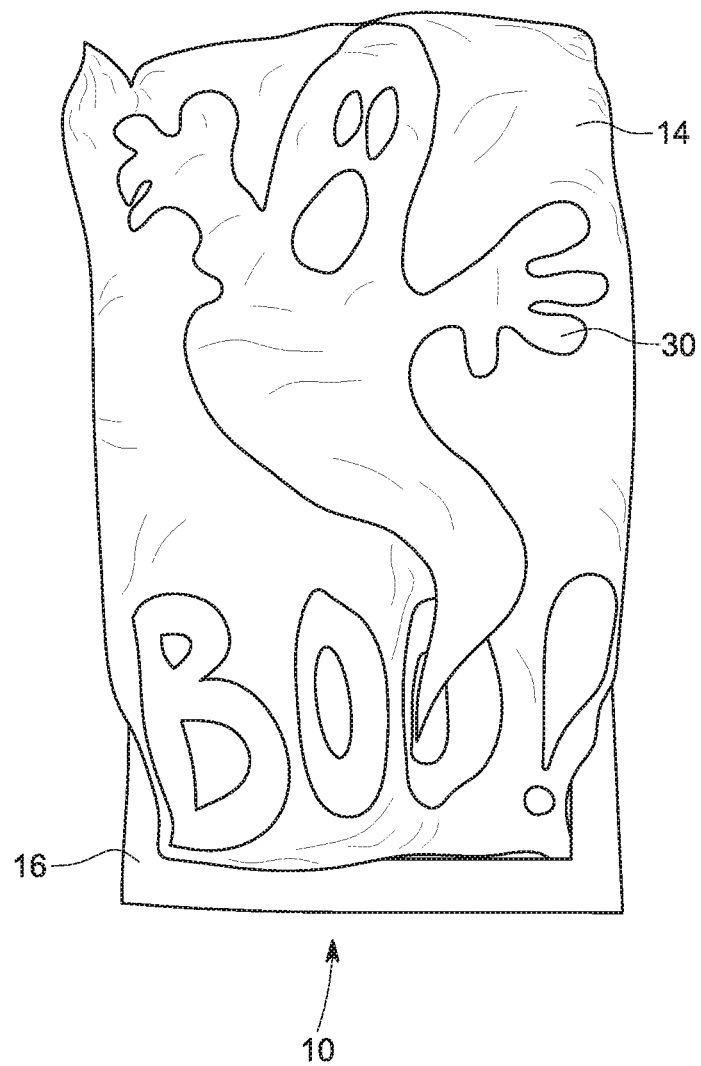
FIG. 7 is a photograph of an assembled vent balloon.

FIG. 6D shows the inflatable body 14 positioned to be attached to the base 16 at the open end. Any protective liners 52 on the inner adhesive 50 along the proximal facing cutout 44 are removed to expose the adhesive. The open end 17 of the inflatable body 14 is pulled through the proximal facing cutout 44 from the proximal side 18 to the inner side 48 and an edge 60 of the open end 17 is secured by the inner adhesive 50 (FIGS. 6E (partly attached) and 6F (completely attached)). In the final step, any protective liners 52 on the inner adhesive 50 along the inner edge 54 and outer edge 56 of the inner distal side 58 are removed. The distal side 22 is folded to meet the proximal side 18 along the center seam 46, as shown in FIG. 6G, resulting in the assembled vent balloon 10.

The removable adhesive 20 on the distal side 22 of the base 16 can be covered by removable protective strips 21 that protect the removable adhesive 20 until the vent balloon 10 is used. The removable adhesive 20 remains attached to the distal side 22 but allows the distal side 22 to be easily removed from the air vent 12, and can be used on any type of air vent 12, including wood, plastic, and painted air vents 12. The removable adhesive 20 can also be reusable once the vent balloon 10 has been removed. The removable adhesive 20 can optionally be magnetic tape that can secure to steel vents with magnetic force.

The present invention also provides for a method of using the vent balloon 10, by removably adhering the inflatable body 14 through the base 16 to an air vent 12, flowing air through the inflatable body 14, and inflating the inflatable body 14. More specifically, the distal side 22 of the base 16 is removably adhered to the air vent 12. Once the vent balloon 10 is inflated, the inflatable body 14 stands upright and the design 30 is displayed and visible. A portion of the air also flows through vents 28 out of the inflatable body 14 such that the vent balloon 10 maintains its inflated shape without lifting off of the air vent 12. The vent balloon 10 can include any of the features described above, and can use a lay-flat polyethylene bag or gusseted polyethylene bag, and include any design. The vent balloon 10 can also be initially folded, obscuring or hiding the design, and once placed over the air vent 12, the inflatable body 14 unfolds and inflates to reveal the design 30, especially to reveal a surprise message.

Figure 10:
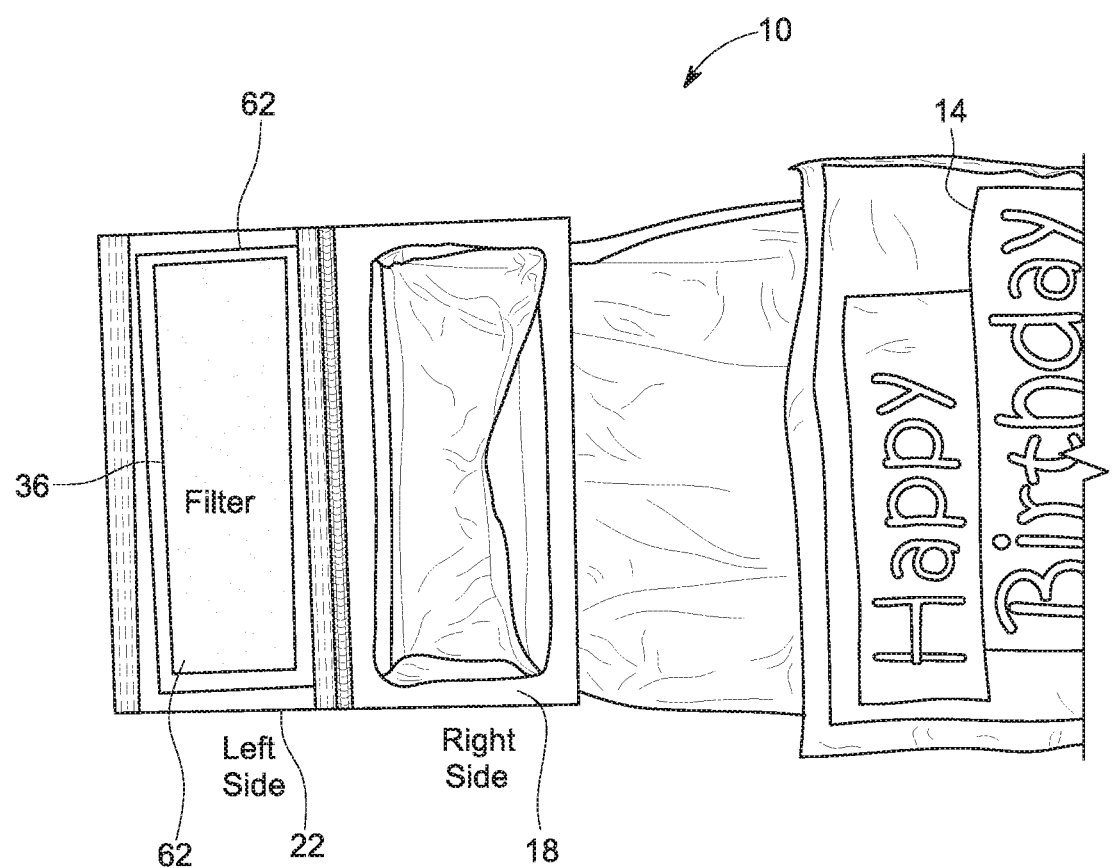
FIG. 10 is a view of a filter/scent mechanism with the base.
Figure 12:
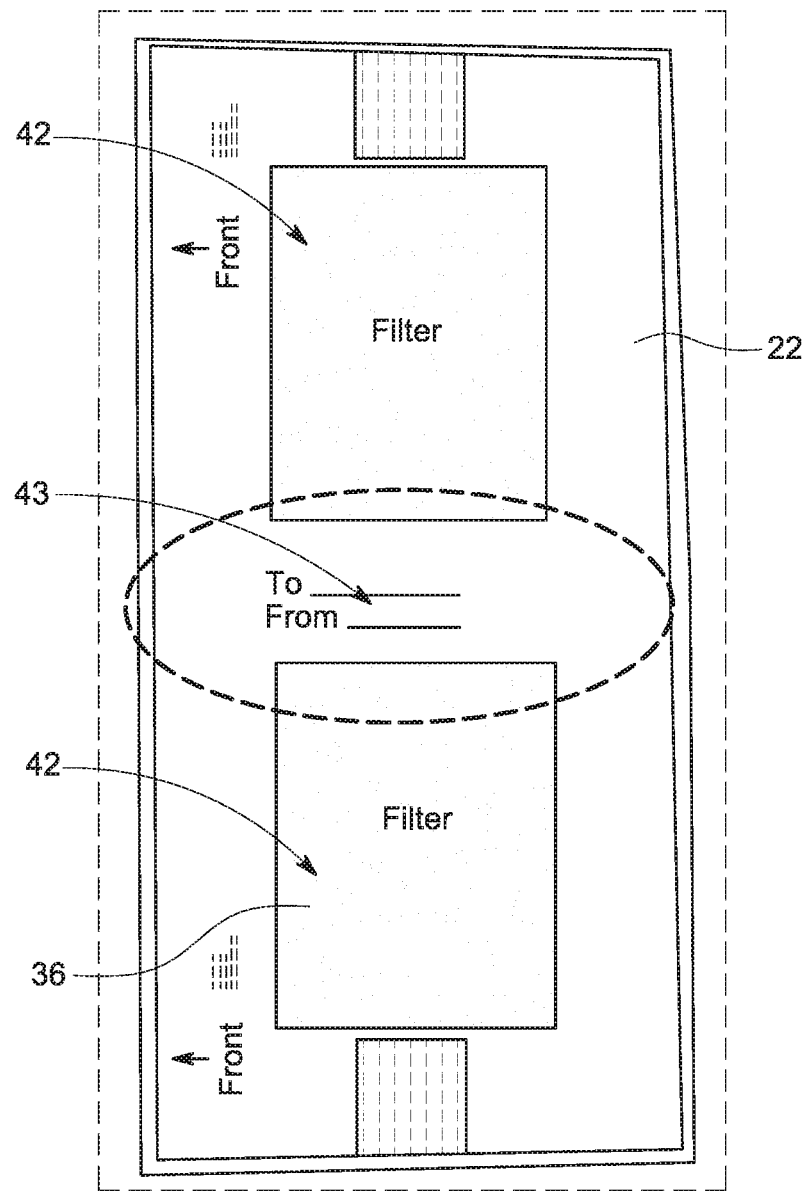
FIG. 12 is a bottom view of a filter/scent mechanism in the base.

The vent balloon 10 can also further include at least one filter or scent mechanism 36, shown in FIG. 10, that is activated upon air flowing through the vent balloon 10 from the air vent 12 and out through the vents 28 to disperse scent in a room. The filter/scent mechanism 36 can be operatively attached with a filter adhesive 62 in any suitable location, such as on the inner side 48 of the base 16 (shown in FIG. 10) or on an inside 38 of the inflatable body 14. After attaching the inflatable body 14 as in FIG. 6F, the filter/scent mechanism 36 can be attached to the filter adhesive 62 (after removing any protective liner 52), and then the distal side 22 folded to meet the proximal side 18 as in FIG. 6G. The central bar 43 provides support to the filter/scent mechanism 36, as shown in FIG. 12. The filter 36 can be unscented, or the scent mechanism 36 can include a scent related to the design 30, such as a pumpkin spice scent for a Halloween or fall design, a peppermint scent for a Christmas design, a rose or peppermint scent for Valentine's Day or anniversary design, a rose scent for Mother's Day, or a cake scent for a birthday design. The scent mechanism 36 can include a container holding a gel or oil containing scent therein that releases the scent when air flows past.

A musical chip can also be included on the center bar 43 for music associated with the design 30.

Therefore, the present invention provides for a vent balloon 10 for dispersing scent in a room, including an inflatable body 14 operatively attached to a base 16 on a proximal side 18, a removable adhesive 20 attached to a distal side 22 of the base 16 for attaching to an air vent 12, and at least one scent mechanism 36 operatively attached to the vent balloon 10 for dispersing scent in the room.

The present invention also provides for a method of dispersing scent in a room, by removably adhering the inflatable body 14 of the vent balloon 10 through the base 16 to an air vent 12, flowing air through the inflatable body 14 and over at least one scent mechanism 36, releasing scent into the air, inflating the inflatable body 14, and flowing scented air through vents 28 on the inflatable body 14 into the room. As above, more specifically, the distal side 22 of the base 16 is removably adhered to the air vent 12. Once the vent balloon 10 is inflated, the design 30 is visible. A portion of the air also flows through vents 28 out of the inflatable body 14 such that the vent balloon 10 maintains its inflated shape without lifting off of the air vent 12. The vent balloon 10 can include any of the features described above, and can use a lay-flat polyethylene bag or gusseted polyethylene bag, and include any design.

There are several advantages to the vent balloon 10 of the present invention. When the base 16 is made of plastic, this allows for a UL rating for product liability to be obtained during use over a hot air vent 12. Plastic is also more aesthetically pleasing to the consumer. A flexible plastic base 16 allows the vent balloon 10 to be mailed to the consumer without damage if bent during mail processing and delivery, and also allows for a reduced mailing cost versus an inflatable base due to the size. The vent balloon 10 being lightweight also allows for a low mailing cost.

Throughout this application, various publications, including United States patents, are referenced by author and year and patents by number. Full citations for the publications are listed below. The disclosures of these publications and patents in their entireties are hereby incorporated by reference into this application in order to more fully describe the state of the art to which this invention pertains.

The invention has been described in an illustrative manner, and it is to be understood that the terminology, which has been used is intended to be in the nature of words of description rather than of limitation.

Obviously, many modifications and variations of the present invention are possible in light of the above teachings. It is, therefore, to be understood that within the scope of the appended claims, the invention can be practiced otherwise than as specifically described.

What is claimed is:

1. A vent balloon for use over an air vent, comprising:
an inflatable body operatively attached to a planar rectangular base on a proximal side, wherein an entire open end of said inflatable body forms an airtight seal with said base; and
a removable adhesive attached to a distal side of said base for attaching to an air vent, wherein said vent balloon includes folds for fitting inside an envelope for mailing, said inflatable body having a folded condition inside and outside of the envelope hiding a design disposed thereon, and an unfolded condition when inflated to reveal said design when attached to an air vent, and wherein said distal side and said proximal side of said base are joined at a center seam, wherein said distal side includes two distal facing cutouts separated by a central bar and said proximal side includes a proximal facing cutout, and wherein said inflatable body is secured on an inside of said proximal side with adhesive.

2. The vent balloon of claim 1, wherein said inflatable body is a polyethylene bag chosen from the group consisting of a lay-flat polyethylene bag and a gusseted polyethylene bag.

3. The vent balloon of claim 1, wherein said inflatable body includes a closed end.

4. The vent balloon of claim 1, wherein said inflatable body includes at least one vent for releasing air from said vent balloon.

5. The vent balloon of claim 1, wherein said inflatable body includes said design imprinted on a side chosen from a front side and both a front side and back side.

6. The vent balloon of claim 5, wherein said design is chosen from the group consisting of a holiday greeting, congratulations, a personal message, cartoon characters, general celebratory designs, and promotional advertisements.

7. The vent balloon of claim 1, wherein said base is made of a material chosen from the group consisting of corrugated cardboard, corrugated plastic, and molded plastic.

8. The vent balloon of claim 1, wherein said base fits over a standard air vent.

9. The vent balloon of claim 1, further including removable protective strips covering said removable adhesive on said distal side of said base.

10. A method of using a vent balloon, including the steps of:
removing a vent balloon from an envelope;
removably adhering an inflatable body of the vent balloon through a planar rectangular base to an air vent, wherein an entire open end of the inflatable body forms an air tight seal with the base, and wherein the inflatable body is initially folded and hides a design, and wherein a distal side and a proximal side of the base are joined at a center seam, wherein the distal side includes two distal facing cutouts separated by a central bar and the proximal side includes a proximal facing cutout, and wherein the inflatable body is secured on an inside of the proximal side with adhesive;
flowing air through the inflatable body; and
unfolding the inflatable body, inflating the inflatable body, and revealing the design.

11. The method of claim 10, wherein said removably adhering step is further defined as removably adhering a distal side of the base to the air vent.

12. The method of claim 10, wherein said inflating step includes causing the inflatable body to stand upright and displaying the design on the inflatable body.

13. The method of claim 10, further including the step of flowing a portion of air in the inflatable body through at least one vent in the inflatable body such that the vent balloon maintains an inflated shape without lifting off of the air vent.

14. The method of claim 10, wherein the inflatable body is a polyethylene bag chosen from the group consisting of a lay-flat polyethylene bag and a gusseted polyethylene bag.

15. The method of claim 10, wherein the design is chosen from the group consisting of a holiday greeting, congratulations, a personal message.

16. A vent balloon for dispersing scent in a room, comprising:
an inflatable body operatively attached to a planar rectangular base on a proximal side, wherein an entire open end of said inflatable body forms an airtight seal with said base;
a removable adhesive attached to a distal side of said base for attaching to an air vent; and
at least one scent mechanism operatively attached to said vent balloon for dispersing scent in the room, wherein said vent balloon includes folds for fitting inside an envelope for mailing, said inflatable body having a folded condition inside and outside of the envelope hiding a design disposed thereon, and an unfolded condition when inflated to reveal said design when attached to an air vent, and wherein said distal side and said proximal side of said base are joined at a center seam, wherein said distal side includes two distal facing cutouts separated by a central bar and said proximal side includes a proximal facing cutout, and wherein said inflatable body is secured on an inside of said proximal side with adhesive.

17. The vent balloon of claim 16, wherein said scent mechanism is operatively attached to said base and supported by the central bar on said base.

18. The vent balloon of claim 16, wherein said scent mechanism includes a scent related to said design on said inflatable body.

19. The vent balloon of claim 16, wherein said inflatable body is a polyethylene bag chosen from the group consisting of a lay-flat polyethylene bag and a gusseted polyethylene bag.

20. The vent balloon of claim 16, wherein said inflatable body includes a closed end.

21. The vent balloon of claim 16, wherein said inflatable body includes at least one vent for releasing air from said vent balloon.

22. The vent balloon of claim 16, wherein said inflatable body includes said design imprinted on a side chosen from a front side and both a front side and back side.

23. The vent balloon of claim 22, wherein said design is chosen from the group consisting of a holiday greeting, congratulations, a personal message, cartoon characters, general celebratory designs, and promotional advertisements.

24. The vent balloon of claim 16, wherein said base is made of a material chosen from the group consisting of corrugated cardboard, corrugated plastic, and molded plastic.

25. The vent balloon of claim 16, wherein said base fits over a standard air vent.

26. The vent balloon of claim 16, further including removable protective strips covering said removable adhesive on said distal side of said base.

27. A method of dispersing scent in a room, consisting of the steps of:
removing a vent balloon from an envelope;
removably adhering an inflatable body of the vent balloon through a planar rectangular base to an air vent, wherein an entire open end of the inflatable body forms an air tight seal with the base, and wherein the inflatable body is initially folded and hides a design, and wherein a distal side and a proximal side of the base are joined at a center seam, wherein the distal side includes two distal facing cutouts separated by a central bar and the proximal side includes a proximal facing cutout, and wherein the inflatable body is secured on an inside of the proximal side with adhesive;
flowing air through the inflatable body and over at least one scent mechanism;
releasing scent into the air;
unfolding the inflatable body, inflating the inflatable body, and revealing the design; and
flowing scented air through vents on the inflatable body into the room.

28. The method of claim 27, wherein the scent mechanism is operatively attached to a location chosen from the group consisting of an inside of the inflatable body and the base.

29. The method of claim 27, wherein the scent mechanism includes a scent related to the design on the inflatable body.

30. The method of claim 27, wherein said inflating step includes causing the inflatable body to stand upright and displaying the design on the inflatable body.

31. The method of claim 27, further including the step of flowing a portion of air in the inflatable body through at least one vent in the inflatable body such that the vent balloon maintains an inflated shape without lifting off of the air vent.

32. The method of claim 27, wherein the inflatable body is a polyethylene bag chosen from the group consisting of a lay-flat polyethylene bag and a gusseted polyethylene bag.

33. The method of claim 27, wherein the design is chosen from the group consisting of a holiday greeting, congratulations, a personal message.

\* \* \* \* \*